United States Patent [19]

Lee

[11] 4,215,102
[45] Jul. 29, 1980

[54] CYTOCHEMICAL AGENTS AND METHODS FOR THE DETECTION OF STEROID HORMONE RECEPTORS IN HUMAN TISSUES

[76] Inventor: Sin H. Lee, 53 Milan Rd., Woodbridge, Conn. 06525

[21] Appl. No.: 1,205

[22] Filed: Jan. 5, 1979

Related U.S. Application Data

[63] Continuation-in-part of Ser. No. 947,700, Sep. 29, 1978, abandoned, and a continuation-in-part of Ser. No. 876,564, Feb. 10, 1978, abandoned.

[51] Int. Cl.$^2$ ............... C07G 7/00; C07G 15/00
[52] U.S. Cl. ................................ 424/3; 260/112 R; 260/112 B; 260/113; 260/121; 260/122; 260/123; 260/335; 424/7; 424/8; 424/12; 260/112.5 R
[58] Field of Search ............... 260/112 R, 112 B, 121, 260/122, 123, 113, 335, 112.5; 424/8, 12, 85, 3

[56] References Cited

U.S. PATENT DOCUMENTS

| | | | |
|---|---|---|---|
| 3,304,297 | 2/1967 | Wegmann et al. | 260/335 |
| 3,789,116 | 1/1974 | Kay | 424/7 X |
| 3,996,345 | 12/1976 | Ullman et al. | 424/12 |
| 3,998,943 | 12/1976 | Ullman | 424/12 |
| 4,022,878 | 5/1977 | Gross | 424/88 X |
| 4,133,639 | 1/1979 | Harte | 424/8 X |
| 4,160,016 | 7/1979 | Ullman | 424/12 X |
| 4,166,105 | 8/1979 | Hirschfeld | 424/3 X |

OTHER PUBLICATIONS

Merck Index, 8th ed. 1968, pp. 837, 847.
Synthetic Organic Chemistry, Wagner et al., 1953, pp. 480, 567, 645.
J. Expft. Med. vol. 91, (1950), pp. 1–13, Coons, et al.
J. Biol. Chem. 228:713–727 (1957), Erlanger et al.
Anal. Biochem. 11:272–278 (1965). Tengerdy.
Nature (London), New Biol. 230:219–220 (1971), Fiume et al.
An. Assoc. Quim. Argent. 63:113–140 (1975), Romeu et al.
Biochemistry, 16:2896–2901, (1977), Lee et al.
Am. J. of Pathology, vol. 34, 1958, Riggs et al., pp. 1081–1097.
Steroids, vol. 18, 1971, Dean et al. pp. 593–603.
Steroids, vol. 19, 1972, Lindner et al. pp. 357–375.
Jama, vol. 237, No. 24, p. 2587, Jun., 1977, Pertschuk.
Jama, vol. 238, No. 17, p. 1806, Oct. 1977, Jensen, et al.
Biochemical & Biophysical Research Communications 74:538–544 (1977), Dandliker et al.
Research Communications in Chem. Pathology & Pharmacology 14:103–110 (1976), Dandliker et al.
Research Communications in Chem. Pathology & Pharmacology 14:771–774 (1976), Pertschuk.
Cancer 41:907–911 (1978), Pertschuk et al.
Fed. Proceedings, 37:1312, (1978), Mercer et al.
Proc. Nat. Acad. of Science USA 74:3681–3685 (1977), Greene et al.
Am. J. of Clin. Pathology, 70:197–203, Aug., 1978, Lee.
Am. J. Clin. Path. 71, 504–508 (1979, May), Pertschuk et al.
Proceedings of the Fed. of American Societies for Exp. Biology, Abstracts, # 3608,3609, Apr. 1–10, 1979.

*Primary Examiner*—Howard E. Schain
*Attorney, Agent, or Firm*—Cushman, Darby & Cushman

[57] ABSTRACT

A cytochemical agent and method for the detection and identification of estrogen or progesterone receptor cells in carcinomas of the breast is described, involving an estrogen-protein-fluorochrome conjugate or a progesterone-protein-fluorochrome agent which is applied to an excised unfixed frozen tissue section, which is then examined for the appearance of fluorescent dye staining of the cells therein, for evaluation of potential endocrine or hormone therapy of the patient. Additional cytochemical agents and methods for the detection of other types of hormone receptor cells in various kinds of cancerous tissue are also disclosed, using sex hormones and endocrine steroid components.

17 Claims, No Drawings

CYTOCHEMICAL AGENTS AND METHODS FOR THE DETECTION OF STEROID HORMONE RECEPTORS IN HUMAN TISSUES

BACKGROUND OF THE INVENTION

This application is a continuation-in-part of my two earlier copending application Ser. Nos. 876,564 and 947,700 respectively filed Feb. 10, 1978 and Sept. 29, 1978, both now abandoned.

In recent years, the assay of the estrogen receptor (ER) characteristic in cytosol protein of tumor tissue homogenates has proved to be a useful technique in selecting patients having advanced mammary carcinoma for possible hormonal therapy. See, e.g., N Engl J Med, 291:1252-1253 (1974). Patients selected by estrogen receptor assay have been reported to show an objective remission rate of from 32% to 60% in contrast to only from 20% to 30% response for those patients selected solely by clinical criteria. See, e.g., Cancer, 39:1971-1977 (1977); Cancer Res, 35:3362-3364 (1975); Cancer, 39:2934-2947 (1977); Cancer 23:145-151 (1969) and JAMA, 172:1271-1283 (1960), respectively.

However, the failure to obtain higher response rates among patients whose tumors were interpreted as positive for estrogen receptor, coupled with the fact that about 10% of those patients suffering from breast cancer with no demonstrable estrogen receptor value still responded favorably to a variety of endocrine therapies, indicate that further improvement of the existent methodology is needed for detecting and discriminating potentially hormone-responsive mammary carcinomas.

The current biochemical assay methods measure the estradiol-binding capacity of the proteins in the cytosol fraction of tissue homogenates. Its results are therefore influenced by the actual size of the cancerous mass in the tissue submitted for assay, by the percentage of cancer receptor protein extractable into the cytosol, and by the proteins extractable from other non-cancerous tissue components. Consequently, variations in these factors alone can contribute to the observed wide fluctuations of the final deduced estrogen receptor values, and result in an inaccurate indication of the true physiological states of the cancer cell population.

While, as stated, patients selected by estrogen receptor assay show an objective remission rate of 32% to 60%, this still means 68% to 40% of the patients selected by this method still fail to benefit from hormonal therapy. In order to improve the methodology of selecting patients, the assay of progesterone receptors in the tumor cytosol as a second marker for determination of potentially hormone-responsive breast cancers has been employed.

Progesterone receptors have been reported in 30-60% of breast cancers (In Progesterone Receptors in Normal and Neoplastic Tissue, eds W. L. McQuire, J. P. Raynaud, and E. E. Baulieu, P. 171, New York, Raven Press, 1977). They apparently occur only in tumors which are positive for estrogen receptors (European Journal of Cancer, 13:1205, 1977). Early data seemed to indicate that a finding of both estrogen receptors and progesterone receptors in the same tumor might be expected to correlate more closely with hormonal responsiveness. While one European series did not support such claims, nevertheless, on the basis of these preliminary biochemical assays progesterone receptors may well serve as a second marker for hormone-responsive mammary carcinomas although further investigation is needed to establish the scope of such determinations.

The current biochemical assay of progesterone receptors has the similar difficulties as already discussed for the estrogen receptors. Therefore, there is a similar need for a simple, more accurate cytochemical technique which can measure the percentages of progesterone receptor-positive cells in the cancer cell populations as well as for the estrogen receptors.

Further, other types of carcinoma are also susceptible to hormone therapy and there has generally been a need for an improved agent which will facilitate the detection and identification of hormone receptors in malignant tissue.

PURPOSE AND OBJECT OF THE INVENTION

The purpose and object of this present invention is to develop a direct cytochemical agent and method useful for the investigation and identification of estrogen and/or progesterone or other hormone binding of individual cancer cells, and as an alternative or supplementary predictor for the selection of patients for hormonal therapy.

Basically, the present invention involves the discovery and development of certain hormone-protein-dyestuff conjugate agents which have the striking and advantageous capability of selectively indicating, in a visual way, the presence of the type of mammary carcinoma in a tissue mass, which will potentially undergo remission upon administration of suitable hormone medication to the patient in question. In effect, a chemical tracer is provided by this invention which will detect estrogen and/or progesterone receptors in human mammary cancer cells, isolated and tested in frozen sections. Further, the invention includes the use of other hormone agents for the detection of corresponding receptor cells in various other types of malignancies. The invention promises to constitute a major advance in identifying the type of therapy appropriate to achieve remission of the living carcinomas.

SUMMARY DESCRIPTION OF THE INVENTION

The practice of this invention may be briefly summarized as follows, with the same being first illustrated with regard to estrogen receptors:

A section of tissues containing, or suspected to contain, primary or metastatic mammary carcinoma is removed from the patient by surgery and frozen. Such section is then cut to about 14μ thick and mounted on a microscopic slide, and thereafter dried in a refrigerator (at about 2° to 5° C.) for about 1 hour. Then, after rehydration by a brief rinse in an aqueous phosphate-buffered saline solution (e.g., of 0.85% NaCl containing 0.01 M phosphate, pH 7.4), the tissue specimen is coated with, e.g., a fluorescent estradiol conjugate agent (more fully described below), and then incubated in a humid chamber at ambient room temperature (e.g., about 16° to 22° C.) for about 2 hours.

The conjugate coating is then removed from the tissue specimen, and the section is rinsed gently again in the phosphate-buffered saline; it is immersed in the saline for about 1 hour, advantageously with one change of fresh washing solution, covered with phosphate-buffered glycerine, pH 7.2-7.8 and a slide cover slip, and then examined under a fluorescence microscope.

After such treatment with the fluorescent estradiol conjugate, breast cancer cells in the unfixed frozen sections, when examined with a fluorescence microscope, were readily separated into two major categories, i.e., cancer cells exhibiting a brilliant green color, primarily cytoplasmic fluorescence, and those which did not fluoresce, or did so minimally.

The presence of cellular fluorescence following such treatment is interpreted as a result of the specific binding of estradiol residues of the conjugate, by the tissue, and is accepted as evidence indicating the presence of estrogen receptor therein.

Positive and negative blocking of specific staining of the cellular estrogen receptor was also examined, by pre-incubation of the dried frozen sections, in e.g., a similar estradiol compound but lacking the fluorescent dye component, and in a plain buffered bovine serum albumin ("BSA") solution, respectively for 1 hour, before serial dilutions of fluorescent estradiol conjugate were applied. The sections were incubated, washed and examined as described above.

In order to obtain complete specific blocking, it was found necessary to dilute the fluorescent estradiol conjugate or to use conjugates with low steroid/protein ratios so that the concentration of estradiol residues in the stain would not exceed 1/10 of that in the blocking solutions which had a steroid/protein ratio of 20 to 25. Attempts to use unconjugated 17$\beta$-estradiol or 17$\beta$-estradiol-6-CMO as blocking agents were unsuccessful because in the absence of a protein carrier the solubilities of these chemicals in aqueous solutions of about pH 7.4 were not high enough to saturate the binding sites of ER positive cancer cells.

The fluorescent estradiol conjugate did not stain tissue sections of the vermiform appendices, tonsils, carcinomas of the colon and stomach, which were prepared in the same manner as negative controls.

With respect to progesterone receptor-containing cells, a similar approach is used. The staining technique for preparation of the tissue sections for fluorescence microscopy is exactly the same as for estrogen receptors except in this case a fluorescent progesterone conjugate is used as the cytochemical agent.

DETAILED DESCRIPTION OF THE INVENTION

As the foregoing summary description indicates, this invention provides new cytochemical agents and methods for demonstrating estrogen and/or progesterone binding capacity in frozen sections of human breast tissue. The method depends in turn on successful preparation of a novel receptor tracer consisting essentially of a protein carrier double-labeled with both a hormonal estradiol or progesterone steroid compound, and with a fluorescent dye compound.

The protein carrier appears to be an indispensable component of this tracer since through covalent bonding with its amino-acid residues it carries the steroid into aqueous solution, thus providing concentrations high enough for cytochemical usage.

Other hormonal/steroid components may also be utilized in the combination, as well as multifunctional hydrophilic carriers other than protein.

When a steroid hormone is coupled to peptide carriers, it is essential to keep its physioloical functional groups intact and exposed, if specificity of the hormone in its natural molecular configuration is to be maintained. In the case of 17$\beta$-estradiol, coupling with bovine serum albumin through a chemical handle at the 6-position has already proved successful in preserving its immunological specificity (see, e.g., Steroids, 18:593–603 (1971); Steroids, 19:357–375 (1972)). A somewhat similar approach is employed herein to prepare the conjugate used herein; however, certain procedures have been modified to achieve high molecular dye/protein and steroid/protein ratios. On the average, in the preferred practice of the present invention, about 11 moles of the fluorescent dye and 24 moles of hormone are advantageously attached to one mole of protein, (e.g., "BSA").

The chemical synthesis of the fluorescent progesterone conjugate, as more fully described hereinafter, may be achieved by similarly attaching the progesterone molecule to e.g., the bovine serum albuminfluorochrome dye complex, for instance, either at the 11-position or at the 6-position of the steroid hormone.

MATERIALS AND METHODS

Estrogen Embodiments

Synthesis of 17$\beta$-estradiol-6-(O-carboxymethyl) oxime

As described by Longwell and Wintersteiner, J. Biol. Chem. 133:219–229 (1940), the disclosure of which is incorporated herein by reference, 17$\beta$-estradiol diacetate (10 g) was dissolved in glacial acetic acid (34.5 ml), and a solution of chromium trioxide (8.5 g) in water (6.9 ml) and glacial acetic acid (51 ml) was added thereto. The mixture was stirred at room temperature for 24 hours, diluted to 500 ml with water and extracted four times each with 500 ml of ether. Most of the acetic acid was removed from the combined ether extract by washing it with saturated $NaHCO_3$ solution until a faint pink color appeared in the aqueous phase. The ether phase was then further exhaustively washed with 3:1 mixture of 5% $Na_2CO_3$ and saturated $NaHCO_3$ solutions, and then with water, and then evaporated to dryness. The residue was dissolved in a 1:4 ethyl acetate-petroleum ether (b.p. 60°–100° C.) mixture (200 ml), and passed through a 22×4.5 cm column of silica gel. The column was next eluted with 3 liters of the 1:4 ethyl acetate-hexane; and 200 ml fractions thereof were collected.

Analysis thereof developed a peak of elution of the 6-keto-17$\beta$-estradiol diacetate in fractions obtained prior to the elution of the yellowish, apparently overoxidized, by-products (probably a keto acid and its derivatives).

After evaporation of the eluting solvent, the crude 6-keto-17$\beta$-estradiol diacetate fractions were combined and recrystallized from absolute ethanol, yielding 2.5 g of needle-like crystals (m.p. about 173° C.).

To prepare 6-keto-17$\beta$-estradiol, the 6-keto-17$\beta$-estradiol diacetate (2.5 g) was hydrolyzed in 75 ml of 20% KOH in methyl alcohol under nitrogen for 24 hours at room temperature. A yellowish solution resulted, which was then diluted with water to about 400 ml, acidified with hydrochloric acid to a pH of 2, and extracted three times each with 500 ml of ether. The ether extracts were combined and washed with 5% $Na_2CO_3$ solution saturated with $NaHCO_3$, and then with water. After evaporation to dryness, the crude product was recrystallized twice from absolute ethanol, yielding crystal plates (m.p. about 280° C.; yield 1.5 g).

The general method outlined by Erlanger et al, Methods in Immunology and Immunochemistry, Ed. Williams CA, Chase MW. Academic Press, New York, Vol. 1, 144–159, (1967), the disclosure of which is incorporated herein by reference, was next followed to prepare 17β-estradiol-6-(O-carboxymethyl) oxime. 6-keto-17β-estradiol (1.5 g) was dissolved in ethanol (75 ml) and 2 N KOH (6.8 ml); carboxymethoxylamine hemihydrochloride (94%; 1.5 g) was then added. The mixture was refluxed for 3 hours, and the alcohol was thereafter evaporated. After adding water (150 ml) to dissolve the residue, the solution was adjusted to a pH of 8.5, filtered to remove insoluble particles, if any, and extracted twice each with 30 ml of ethyl acetate. After acidification to a pH of 2 with HCl, a white precipitate was formed. The latter was collected by filtration, dried in a 37° C. incubator, and recrystallized twice from acetone, yielding 1.4 g needles (m.p. 196°–199° C.).

Identification of the 17β-estradiol-6-(O-carboxymethyl) oxime and its precursors was carried out by melting points and thin layer chromatography on silica gel plates (solvent system: ethyl acetate/n-hexane/ethanol/acetic acid at a ratio of 72/13.5/4.5/10). The values were found to be those expected for these chemicals as reported in the literature (e.g., Steroids, 18:593–603 (1971) and 19:357–375 (1972)).

Preparation of fluorescein isothiocyanate (FITC)-bovin serum albumin (BSA) complex (FITC-BSA)

The general procedure of Am. J. Path., 34: 1081–1097 (1958), the disclosure of which is incorporated herein by reference was followed, except that a high FITC-BSA ratio was used. In detail, BSA (1 g; Sigma Chemical Co., crystallized and lyophilized) was dissolved in 10 ml of 0.5 M carbonate-bicarbonate buffer (pH of 9.5). FITC (1 g) on celite (10%, Sigma Chemical Co.) was then added to the solution, followed by stirring for 4 hours at room temperature. After removing the celite by centrifugation, the FITC-BSA complex was passed through a Sephadex G-25 column which has previously been equilibrated with 0.05 M phosphate buffer (pH 7.8) and dialyzed against the same buffer for an additional 48 hours to assure complete removal of any loosely bound FITC. The protein content was determined by the biuret reaction. The average molecular fluorescein/protein ratio was 11.2 (±0.5) calculated from the absorbancy of pure FITC in 0.1 N NaOH at 495 nm.

Preparation of 17β-estradiol-6-CMO-BSA-FITC conjugate (fluorescein estradiol conjugate)

An aliquot of the FITC-BSA complex obtained as described above, and in a phosphate buffer containing protein (200 mg), 1-ethyl-3-(3-dimethylaminopropyl) carbodiimide hydrochloride (200 mg), and 17β-estradiol-6-(O-carboxymethyl) oxime (200 mg) dissolved in 6 ml of dioxane, 5 ml of water and adequate 0.05 M phosphate buffer, at a pH of 7.8 to make up a total volume of 21 ml were stirred for 20 hours at room temperature. In this process, the estradiol is coupled to the BSA by formation of a peptide bond between the ε-amino groups in the "BSA" protein and the carboxyl group of the oxime derivative of the steroid.

The conjugate was then exhaustively dialyzed first against water, and then against a phosphate-buffered saline solution (PBS) (pH 7.4) for 48 hours, and centrifuged (28,000×g, 15 min.). The supernatant liquid was collected, and sodium azide added to a final concentration of 1 mg/ml as preservative.

This solution was further diluted to the desired concentration with PBS before use.

The breast cancer tissue specimens to be examined may be prepared as frozen sections, as described above. They must also be kept in an unfixed state. For instance, if tissue sections which contain estrogen-receptor (ER) positive cancer cells are subjected to fixation in cold acetone (−20°), 3.7% buffered formaldehyde, or 1% glutaraldehyde, this can result in complete abolishment of the cellular estrogen binding capacity.

Further, in order to study the effects of storage on cellular estrogen receptors, separate tissue blocks taken from the ER positive tumors were left in PBS at 2° to 5° C. and frozen at −20° C., respectively. Frozen sections were cut from samples of these blocks at 24 hours intervals, and stained for detection of estrogen receptor. It was found that there was no appreciable loss in the estrogen binding capacity of the cancer cells within 24 hours when tissue blocks were unfrozen and stored at 2°–5° C., but at 72 hours considerable losses were observed, resulting in an apparent low proportion of ER positive cancer cells in the population. Tissue blocks frozen at −20° C. were found to be unsuitable for cytochemical studies; repeated freezing and thawing apparently led to dissociation of estrogen receptor proteins from the tissue sections.

For the practice of this invention, the tissue section must be prepared and studied with the above parameters in mind.

Thus, it is apparent that the cellular estrogen receptors cannot survive even a brief exposure to acetone and aldehyde fixatives. Hence, only unfixed frozen sections are recommended for this technique. Drying the sections on slides in a refrigerator for 1 hour prior to incubation with the fluorescent estradiol conjugate is an accepted compromise since working with unfixed wet frozen sections presents great technical difficulties.

Needless to say, the best timing to obtain materials for cytochemical studies is when routine diagnostic frozen sections are being prepared. Adjacent consecutive sections can be stained with the hematoxylin and eosin method for identification of the cell population. However, if the specimens must be transported, it is recommended that the tissue blocks be kept at 2°–5° C., and be processed within 24 hours. Repeated freezing and thawing may lead to losses of estrogen receptor activity. Postmortem changes taking place during prolonged storage have similar adverse effects.

Application of this cytochemical method on clinical biopsy materials is illustrated by a study of breast lesions, including 17 primary infiltrating duct carcinomas, 2 metastatic mammary carcinomas in axillary lymph nodes, 3 fibroadenomas, 10 cases of benign "fibrocystic mastopathy", and one case of male gynecomastia, all from different patients.

For routine staining of these tissue specimens, the dialyzed fluorescent estradiol conjugate obtained as described above was diluted with PBS (pH 7.4), to a final concentration equivalent to 0.5 μM (±10%) FITC per ml. Such dilutions should show a 17β-estratiol-6-CMO:FITC molecular ratio of 2.2 (±10%), as indicated by the absorbancy (in 0.1 N NaOH) at 340 nm and 495 nm respectively, using the unconjugated oxime and pure FITC in 0.1 N NaOH as standards. No free hormone or fluorescein dye in these solutions was detected on thin layer chromatography.

Among all of the 19 breast cancer cases thus studied, only two carcinomas (one primary and one metastatic) consisted of an almost homogenous population of strongly ER positive cancer cells which were characterized by coarse heavy deposits of the fluorescent estradiol conjugate in the cytoplasm, and to a lesser extent in the nuclei. The concomitant lymphocytes, polymorphonuclear leukocytes, histiocytes, plasma cells, blood vessels and the intervening dense fibrous connective tissue did not exhibit any specific fluorescence.

The other fifteen breast carcinomas (14 primary and 1 metastatic) studied were composed of cancer cells showing varying degrees of fluorescence, ranging from completely negative cells to strongly positive cells, indicating different hormone-binding capacities among different tumors as well as among individual cells of the same tumor. The nuclei of cancer cells were either unstained or stained with much less intensity than the cytoplasm. Only two primary carcinomas were found to be almost entirely composed of unstained cancer cells, and could be interpreted as ER negative tumors. However, even in these latter cases careful search eventually revealed isolated small clusters of ER positive cancer cells.

Benign epithelial cells of the mammary ducts and lobules also showed uneven estrogen binding capacity. The density of fluorescent deposits in these nonneoplastic cells was far below that observed in most ER positive cancer cells, with the majority of epithelial cells being ER negative or containing so few ER sites that they could not be detected by this technique. Little or no estrogen binding capacity was observed in the myoepithelial cells and the adjacent fibrous connective tissue. This picture was quite constant, even in those regions surrounded by ER positive cancer cells. The benign epithelial cells which showed definite estrogen binding were conveniently used as "weakly positive" controls in the tissue sections when intensity of fluorescence among individual tumor cells was graded.

The findings on fibroadenoma and gynecomastia were similar in that both lesions seemed to contain proliferative ductal epithelial cells with moderately increased estrogen binding capacity, and also in that there were stromal cells with definitely demonstrable estrogen receptors surrounding the proliferating ducts in both of these conditions.

The FITC-BSA complex, alone, diluted to a concentration equivalent to 0.5 $\mu$M FITC/ml, was also used as a negative nonspecific staining control. This material failed to stain the ER positive cancer cells. The specificity of this cytochemical technique is supported by the fact that the conjugate fails to stain some well known "non-target" tissues, including the vermiformm appendices, tonsils and carcinomas of the gastrointestinal tract, and that the staining of the target cells (ER positive breast cancer cells) can be blocked by non-fluorescent 17$\beta$-estradiol-6-CMO-BSA. It requires about 10 times non-fluorescent steroid concentration to completely block the specific staining, which is consistent with observations that approximately a 100-fold excess of non-radioactive estradiol is needed to suppress binding of $^3$H-estradiol by the 8S cytosol protein receptors (See J. Clin. Enocrinol. Metab. 37:986–989 (1973).

It has been generally assumed that when malignant transformation occurs, breast cancer cells may retain all or part of the normal population of hormonal receptors, thus developing into ER positive tumors. However, it is also well known that benign mammary tissues rarely contain sufficient estrogen receptors detectable by biochemical assays, see Cancer Res., 30:692–698 (1970). Consequently, it is difficult to explain the high estrogen receptor values found in some of the ER positive cancers with this "retaining" theory. The findings of the present cytochemical study indicate that the ER positive cancer cells not only retain, but often actually acquire higher than normal estrogen binding capacities, possibly in the magnitude of hundred or thousand times that of their benign progenitors. In the breast tissue of female patients of middle and advanced ages, only a small number of the epithelial cells lining the ducts and lobules show any significant degree of estrogen binding.

The results of the practice of this invention also indicate that breast cancers cannot be simply classified as either ER positive or ER negative tumors, because the majority of them are composed of a heterogenous population of cancer cells of different estrogen receptivity with both ER positive and ER negative cells mixed in varying proportions. Perhaps one can always find ER negative cells in any ER positive tumor and vice versa. Therefore, it appears more appropriate to grade breast cancers according to the percentage of ER positive cells in the cancer cell population.

Obviously, comparative studies of the cytochemical data obtained on tumors removed before and after hormonal therapy will provide further informaton on questions of profound importance concerning cancer cell biology. For example, if endocrine treatments are capable of reducing the percentage of ER positive cells in a cancer cell population, it would serve as strong evidence for the linkage between hormonal dependency and hormonal receptivity of malignant cells in general. It could also explain why some ER positive tumors show only partial or short term remissions during hormonal therapy before progressing to a completely autonomous condition. See Cancer, 39:2934–2947 (1977). A concept of a continuous gradient of hormonal dependency extrapolated to the so-called receptor-negative tumors has already also been proposed, Cancer, 39:1971–1977 (1977). The use of the present invention enables observations to be made which aid such studies, e.g., this invention has demonstrated that most mammary carcinomas do in fact contain ER positive cancer cells, and is helpful to identify cancers of breast when dealing with malignancies of questionable origin.

Further, it has been occasionally speculated that endogenous estrogen, circulating in the patient's body fluids, might occupy or even saturate the estrogen receptor sites of a tumor, and thus interfere with receptor assays. The lack of homogenous estrogen binding among individual cancer cells as shown in the practice of this invention and as described above, appears to discount this as a major obstacle to measuring the true estrogen receptivity of a tumor. (However, this does not exclude a possible role by hormones produced locally within the tumor, leading to uneven saturation of individual cells).

The cytochemical data obtainable by the practice of this invention also support the observation that fibroadenoma and breast tissue of male gynecomastia do contain increased estrogen receptivity which can now be detected in both the epithelial and stromal cells.

As will be understood, this invention has been described and illustrated, by example, with specific reference to the use of the 17$\beta$-estradiol-6-(O-carboxymmethyl) oxime/bovine serumm albumin/fluorescein isothiocyanate conjugate. The molecular structure of this conjugate agent may be illustrated as follows:

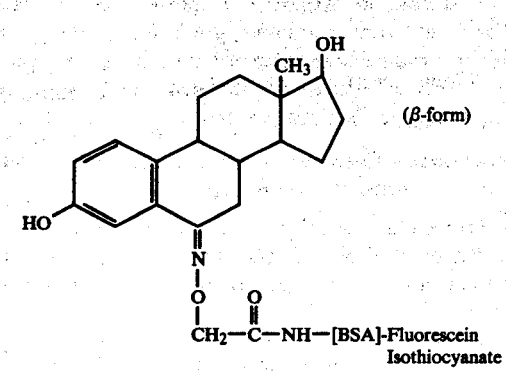

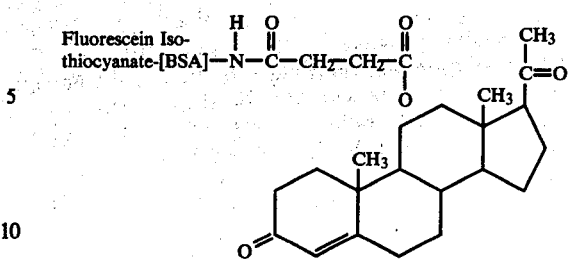

Progesterone Embodiments

As indicated above, the invention may also be practiced using a progesterone-protein-dye conjugate, and methods for this embodiment will now be described and illustrated.

Method I: 11-Position Progesterone Coupling

Synthesis of 11α-Hydroxyprogesterone Hemisuccinate

According to the general principles outlined by Erlanger et al. (Method in Immunology and Immunochemistry Vol. I, p. 148, Ed. C. A. Williams and M. W. Chase. Academic Press N.Y., 1967), and by Buzby et al. (J. Med. Chem. 10:199, 1967), a solution of 11α-hydroxyprogesterone (10 g) (Sigma Chem. Co., St. Louis, MO) and of succinic anhydride (10 g) in dry pyridine (100 ml) was prepared and refluxed under nitrogen atmosphere for 20 hours. The cooled reaction mixture was poured into cold aqueous hydrochloric acid (3 N, 500 ml) containing crushed ice, and extracted with chloroform. After evaporation of the chloroform, the residue was recrystallized repeatedly from acetone-hexane, and from acetone yielding 4.5 gm of white crystals, melting point 148°–152° C. Absorption maximum in 0.1 NaOH was at 243 nm. These characteristics were consistent with those described in the literature (Lindner et al., Steroids 19:357–375, 1972) for 11α-hydroxyprogesterone hemisuccinate.

Preparation of FITC-BSA Complex

The same method as described above may be employed again.

Preparation of 11α-hydroxyprogesterone Hemisuccinate-BSA-FITC (Fluorescent Progesterone-11-Conjugate)

The same coupling procedure as described above for preparation of fluorescent estradiol conjugate may again be used, except that 11α-hydroxyprogesterone hemisuccinate is used in place of 17β-estradiol-6-(O-carboxymethyl) oxime.

The structure of the resulting final conjugate is shown as follows:

The number of steroid residues attached to this final fluorescent progesterone-11-conjugate was determined by dinitrophenylations, using the method according to Erlanger et al. (J. Biol. Chem. 228:713, 1957). On the average, 11 moles of fluorescein dye and 26 moles of hormone are attached to one mole of bovine serum albumin.

The specificity of this technique is supported by the facts that the staining of progesterone receptors in the cancer cells with the fluorescent progesterone conjugate was successfully blocked by pre-incubation of the tissue sections in a nonfluorescent 11α-hydroxyprogesterone hemisuccinate-bovine serum albumin complex, and that the fluorescent progesterone conjugate failed to stain the well-known nontarget tissues, such as the tonsils, vermiform appendices, lymphoid tissues and carcinomas of gastrointestinal tract.

Method II: 6-Position Progesterone Coupling

Synthesis of 6-Bromoprogesterone

According to the method of Sondheimer et al. (J. Am. Chem. Soc. 75:4712, 1953), progesterone (10 g) and N-bromosuccinimide (6 g) were refluxed in carbon tetrachloride (250 ml) for one hour. The mixture was then filtered, and the solvent evaporated. Trituration of the residue with hexane yielded 4 gm of 6-bromoprogesterone, melting point 139°–142° C. Repeated crystallization from acetone-hexane led to an analytical sample with melting point 141°–144° C.

Synthesis of Progesterone-6-(carboxymethylene) thioether

According to the method of Lindner et al (Steroids 19:357, 1972), 6-bromoprogesterone (2.4 g) and thioglycolic acid (0.8 g) were added to methanol (100 ml) containing KOH (1 g). The mixture was refluxed for two hours. After evaporation of most of the methanol, the residue was then diluted with water (100 ml), acidified with HCl (10%) to pH 1 and extracted with ether. The ether phase was then extracted with aqueous NaHCO₃ (0.1 N). Acidification of the alkaline extract with HCl (10%) yielded a precipitate which was collected by filtration, washed with water, dried, and recrystallized from ethyl acetate-petroleum ether. The final product (0.55 gm) had a melting point of 146°–149° C.

Preparation of Progesterone-6-(carboxymethylene) thioether-BSA-FITC (fluorescent progesterone-6-conjugate)

A mixture of progesterone-6-(carboxymethylene) thioether (100 mg) in dimethylformamide (9 ml) and 1-ethyl-3-(3-dimethyl-aminopropyl) carbodiimide hydrochloride (100 mg) in water (10 ml) was stirred for 20 minutes at room temperature, and was added to an aqueous solution of bovine serumm albumin-fluorescein isothiocyanate (10 ml) which contained 100 mg of protein equivalent, without phosphate buffer. It was stirred for 3 days at 4° C., then dialyzed for one day against a solution of NaHCO₃ (0.05 M) and for an additional two days against phosphate-buffered sline, (pH 7.4). The final conjugate was centrifuged to remove the precipitates. Sodium azide was then added to the supernatant liquid to a concentration of 1 mg/ml, as preservative.

The structure of the final conjugate is shown as follows:

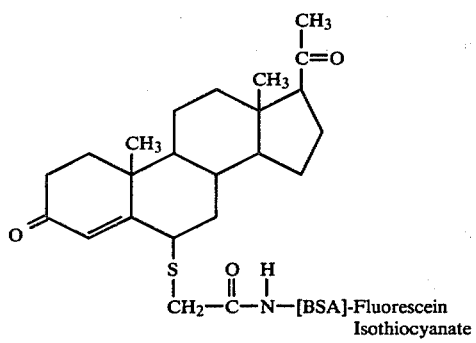

The number of steroid residues attached to the final fluorescent progesterone-6-conjugate was determined by dinitrophenylation, according to the method of Erlanger et al. (J. Biol. Chem. 228:713, 1957). On the average, 11 moles of fluorescein dye and 26 moles of hormone are attached to one mole of bovine serum albumin.

The procedure for use of fluorescent progesterone-6-conjugate to detect cancer cell progesterone receptors is the same as described for fluorescent estradiol conjugate and fluorescent progesterone-11-conjugate.

Specificity of the staining is again supported by blocking technique, using nonfluorescent progesterone-6-BSA complex or nonfluorescent progesterone-11-BSA complex, and by failure of the conjugate to stain nontarget tissues, as mentioned hereinabove.

The successful preparation of these two fluorescent progesterone conjugates, one at the 11-position and the other at the 6-position demonstrates the potential of the cytochemical approach for detection of hormone receptors on human tissues. With a protein carrier, the concentrations of the steroid hormones in the fluorescent conjugates reach one hundred thousand to one milion times the physiological concentration in the human body fluids. This high concentration is a necessity since mere fluorescein-steroid compounds which are hardly soluble in aqueous solutions at physiological pH range cannot be usefully employed as cytochemical receptor tracers.

Of these two fluorescent conjugates, 11α-hydroxyprogesterone hemisuccinate-BSA-FITC (Method I) is easier to prepare, and the yield is higher because a significant amount of protein is denatured during the last stage of preparation for progesterone-6-(carboxymethylene) thioether-BSA-FITC (Method II). However, both approaches can be used to prepare usable progesterone receptor tracers. This is consistent with the immunological observations that either the B ring (6-position) or the C ring (11-position) can be used as chemical handles without affecting the specific functional groups of the steroid hormone-progesterone.

Initial studies on twelve human breast cancers by this applicant have also interestingly shown that progesterone receptors are primarily located in the cytoplasm of the tumor cells, and appear to occur in cancers that also contain estrogen receptor positive cancer cells. Whether progesterone receptors and estrogen receptors always occur accompanying each other and are present in the same cells, has not yet been fully established.

Simultaneous Detection of Estrogen Receptor And Progesterone Receptor Cells

A further example of the practice of this invention is provided by the following illustration of the simultaneous detection of estrogen receptor and progesterone receptor cells:

As reagents there is used

Reagent A. 17β-estradiol-6-CMO-BSA-FITC prepared as outlined hereinabove (at page 10 of this application).

Reagent B. 11α-hydroxyprogesterone hemisuccinate-BSA-tetramethylrhodamine isothiocyanate.

This reagent is prepared according to the same method described above for 11α-hydroxyprogesterone hemisuccinate-BSA-FITC, except that tetramethylrhodamine isothiocyanate is used in place of fluorescein isothiocyanate.

Reagent A and Reagent B are next mixed on an equimolar basis so that the resulting mixture contains $10^{-4}$ to $10^{-3}$ M of bound estradiol and about the same concentration of bound progesterone. The average molecular ratio of steroid hormone components to fluorochrome dyestuff units is thus between about 2:1 and 6:1, generally about 4:1.

Method of Staining

Next, a section of tissue to be studied is cut and stained with the said mixture of reagents A and B, using the same principles as outlined hereinabove under the heading "Summary Description of the Invention".

The thusly-stained tissue section is then examined with a fluorescence microscope equipped with two sets of filters, one selective for fluorescein isothiocyanate excitation and the other selective for rhodamine isothiocyanate excitation. The advantage of using such filters is that the estrogen receptor sites manifest a brilliant green fluorescence while now the progesterone receptor sites show a bright orange-red fluorescence. With this technique, using the aforesaid mixture, the presence of both the estrogen receptor and the progesterone receptor can be simultaneously detected and visually studied in the same tissue specimen.

Results

Using the foregoing embodiment of this invention, twelve cases of breast cancer and three cases of endometrial cancer have been studied with this combined receptor assay technique. The study has confirmed the observation that most estrogen-receptor positive cancer cells do indeed also contain progesterone receptors although the binding capacity of a single cancer cell for the individual hormones may not be at the same level. Benign stromal cells which may show a weak estrogen binding do not seem to have progesterone binding capacity in the female breast. One endometrial cancer had very strong stromal progesterone receptor activity but without concomitant estrogen binding in the stroma.

These results further substantiate that fluorescent steroid hormones when coupled as three-part conjugate molecules can be used to study and identify receptors other than estrogen receptor and also in tissues other than breast cancer.

The successful experience with synthesis of fluorescent progesterone conjugates also indicates and illustrates that the practice of this invention includes the use of three-part conjugates of other natural and synthetic steroidal hormones; for example, androgenic hormones, such as testosterone, and adrenocortical hormones, such as 17α-hydroxycorticosterone (i.e., hydrocortisone, cortisol). Experimental procedures for the preparation of the testosterone-protein-dye and cortisol-protein-dye conjugates are illustrated as follows:

Preparation of Several Fluorescent Testosterone Conjugates (Fluorescent Testosterone Conjugates)

Method I: 11-Position Testosterone Coupling

11α-hydroxytestosterone-11-hemisuccinate may either be purchased from, e.g., Steraloids, Inc., Wilton, N.H., or may be synthesized according to Bosch (Steroids, 23:699–711, 1974).

The preparation of 11α-hydroxytestosterone-11-hemisuccinate BSA-FITC (fluorescent testosterone-11-conjugate) is next accomplished using the same procedure as for preparation of the fluorescent progesterone-11-conjugate described above, except that 11-hydroxytestosterone-11-hemisuccinate is used in place of 11α-hydroprogesterone hemisuccinate.

The structure of the resulting final conjugate may then be shown as follows:

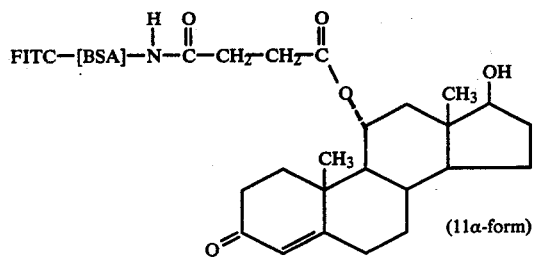

Method II: 7-Position Testosterone Coupling

Testosterone-7α-carboxyethyl thioether may be prepared according to the method described by Weinstein (Steroids, 20:789–812, 1972).

Preparation of testosterone-7-(carboxyethyl) thioether-BSA-FITC (fluorescent testosterone-7-conjugate) is then accomplished using 1-ethyl-3-(3-dimethylaminopropyl) carbodiimide hydrochloride as the coupling reagent, in a medium containing dimethylformamide. The detailed procedure follows that described above as Method II for "6-position progesterone coupling", except that in this case testosterone-7α-carboxyethyl-thioether is used in place of the progesterone-6-(carboxymethylene) thioether.

The structure of the resulting final conjugate may then be shown as follows:

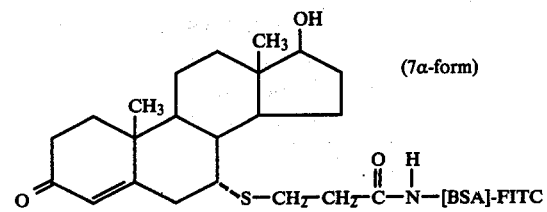

Preparation of Cortisol-3-(O-Carboxymethyl) Oxime-BSA-FITC Conjugate (Fluorescent Cortisol Conjugate)

Cortisol-3-(O-carboxymethyl) oxime may be synthesized using the procedure described by Arnold and James (Steroids 18:789, 1971), and as modified by Fahmy et al (Steroids 26:267, 1975).

Preparation of the cortisol-3-CMO-BSA-FITC may then be accomplished using the same procedure as initially described above for 17β-estradiol-6-CMO-BSA-FITC conjugate except that cortisol-3-(O-carboxymethyl) oxime is used in place of the 17β-estradiol-6-(O-carboxymethyl) oxime.

The structure of the final conjugate may then be shown as follows:

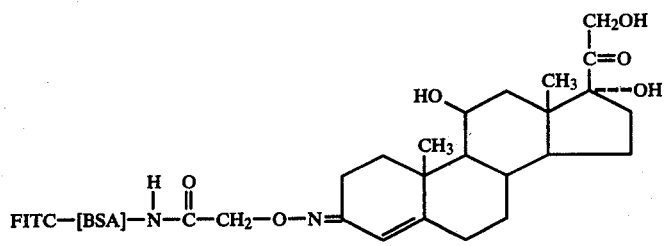

The number of FITC molecules attached to the final fluorescent conjugates containing testosterone or cortisol may be calculated from the absorbancy of the conjugates in 0.1 N NaOH at 495 nm. The number of steroid residues attached to the final conjugates can be determined either by dinitrophyllation, using the method of Erlanger et al. (J. Biol. Chem. 228:713, 1957), or by amino-group determination with trinitrobenzene sulphonic acid (Clin. Chem. 16:24, 1970). Each molecule of bovine serum albumin of the conjugates carries from 20 to 30 testosterone or crotisol residues, and from 4 to 11 molecules of fluorescein in order to ensure a high steroid: dye ratio and a high concentration of effective bound steroid hormones in solution.

Experience accumulated to-date has shown that in order to use the fluorescent steroid hormone conjugates to trace receptors in frozen tissue sections the three-part conjugate should carry an adequate number of steroid residues to maintain a high affinity toward the receptors, whereas the number of fluorochrome dyestuff molecules attached to the carrier unit is not very crucial. In the case of using bovine serum albumin as a carrier, the figures generally fall within the range of about 2:1 to 1:25 or even to 1:50 (fluorochrome:hormone).

The application of the fluorescent testosterone and fluorescent cortisol conjugates on prostatic tissues and hematopoietic tissues is then conducted according to the same general methods already described.

ADDITIONAL EMBODIMENTS OF THE INVENTION

It will, of course, be appreciated, however, that variations in the formulation of such agents may be employed, and that, within the scope of this invention, one can use other complex combinations of hormone-carrier-fluorochrome dyestuffs, so long as there is present in the agent the essential characteristics of (a) a suitable hydrophilic carrier component capable of forming, e.g., a peptide linkage with a carboxyl group or the like, (b) an active hormone agent, having a suitable chemical handle for coupling to said carrier (e.g., an estrogen in the form of a hemisuccinate or a carboxymethylene thioether derivative, or similarly a testosterone or cortical hormone derivative, etc.) and (c) a fluorochrome dyestuff coupled to the aforesaid protein component.

Various specific modifications of the embodiments illustrated above may be employed as will be appreciated by those skilled in the art.

For instance, other protein carrier components may be chosen provided they contain amino groups having the capability of coupling both with the hormone component and with the fluorochrome dye, i.e., those proteins and like chemical compounds which contain a plurality of amino groups. As examples of such alternate protein carriers, the following may be named.

---

Simple proteins: Albumins, globulins, glutelins, prolamines, albuminoids histones and protamines.

Conjugated proteins: Nucleoproteins, glycoproteins, mucoproteins, phosphoproteins, chromoproteins, lipoproteins and metalloproteins.

Derived proteins: Proteins denatured by physical and chemical means. Proteoses, peptones, peptides, diketopiperazines-cyclic anhydrides of two amino acids.

---

Polypeptides derived from amino acids, containing at least two primary amino($-NH_2$) groups, may also be used in place of the protein per se provided that the resulting conjugate will have sufficient solubility.

In addition and alternatively, other hydrophilic molecules such as those possessing multiple hydroxy groups, e.g., polyglycols or polyglycerols, can be used as carriers (with coupling therewith through e.g., ester or ether linkages).

While presently fluorescein is itself a dyestuff of choice to use, a number of other fluorochrome dyes may also be employed, provided only that they comply with the basic requirements of (1) suitably visible fluorescent properties retained in the use described herein, and (2) the capability of coupling with the aforesaid poly-amino-type protein carrier materials. Among such fluorochrome dyes which may thus be employed are the following:

Auramine O, Rhodamine B, Rhodamine 3G, Acriglavine, Acridine orange, Coriphosphine, Acridine yellow, Phosphine, Benzoflavine, Thioflavine TCN, Rhodindine, Magdala red, Berberine, Quinacrine, Rivanol, Tetracycline, Thiazine red R, Thiazole yellow G, Congo red, Acid fuchsin, Sulforhodamine B, Eosin Y, Primuline, Thioflavine S, Tetramethylrhodamine and dinaphtylaminesulfonic acid.

Further, other estrogenic hormones may be employed in place of the 17β-estradiol. That is, estradiol is only one (although the most important form) of the estrogens, and the significant requirement for the practice of this invention is to employ an estrogen to which the cancer cells in question are receptive. As other such compounds, there can, of course, first be mentioned 17α-estradiol, in the form of its 6-(O-carboxymethyl) oxime derivative. This compound conforms to the 17β compound employed in the above Examples, but with the hydroxyl group of the hormone at the 17 position below the plane of the steroid ring. Basically, any of the estrogenic steroid hormones, containing the cyclopentenophenanthrene nucleus, and having the capability of forming the 6-O-carboxymethyl oxime derivative may suitably be employed in place of the estradiol in the foregoing description of this invention, including estriol, estrone and like compounds.

Similarly, other progesterone hormones may be employed including the natural progestional hormones, such as progesterone, pregnanediol, pregnanetriol and pregnanolone, and the synthetic progestins, including compound R5020, Norethindrone, Norethynodrel, etc. All of these compounds may be coupled to the peptide carrier via the chemical linkage at the 6-position or at the 11-position through the same approaches outlined above for progesterone.

It will thus be clear that this method of using a three-part molecular conjugate to trace hormone receptors in cancer cells is adaptable to synthesize fluorescent conjugates containing progesterone, testosterone and cortisol (an adrenal cortical hormone, also known as hydrocortisone) suitable to trace and detect their corresponding receptors under a fluorescence microscope.

The illustrative examples hereinabove include, for example, the use of two female sex hormones (estradiol and progesterone), a male hormone (testosterone) and an adrenal cortical hormone (cortisol), but the invention should not be construed as limited thereto.

While the foregoing are the most important steroid hormones produced naturally in the ovaries, testicles and the cortex of the adrenals, there are numerous hormonal precursors, hormonal metabolites and hormonal analogs, which have been isolated from the mammals or synthesized chemically and can exert physiologic functions similar to those caused by the steroid hormones produced by the ovaries, testicles and adrenal cortex. Obviously, it is impossible to exhaustively list all of the chemicals which may be used in substitution for the estradiol, progesterone, testosterone and cortisol exemplified above, but those skilled in the art will recognize that this invention extends in its broadest concept to the use of all of the other natural and synthetic estrogens, natural progesterone and synthetic progestational agents, and natural and synthetic adrenocortical steroids or steroid analogs in the formation of the three-part conjugate, which are suitably reactive for detection of the corresponding receptors in, e.g., human malignant tissue. (See, for instance, illustrations of such compounds at pages 436–437 and 444 of "Review of Physiological Chemistry", by Harold A. Harper. 11th edition. Lange Medical Publications, Los Altos, Calif., 1967).

Moreover, chemical handles which are used to link up with the protein carrier may be located at the 3-, 6-, 7α-, and/or 11α-positions of the steroid molecules in order to preserve the most important natural physiologic functional groups and the molecular configuration of the hormone. However, this chemical handle can also be placed at another site on the steroid hormone, including but not limited to the 9α-, 17-, and 21- positions of the molecule.

Also, as noted above, there may be conveniently used those conjugates in which there is present at least one fluorochrome dye molecule and at least one hormone molecule attached to the protein molecule in the conjugate. It is desirable to have a ratio of hormone molecules to dye molecules in excess of one in order to enhance the affinity of the conjugate to the tissue receptor. Consequently, the molecular ratio of fluorochrome to hormone should be within the limits of about 2:1 to 1:25, and preferably of about 3:2 to 1:10 and can be about 2:1 to 1:50.

Also, with protein carriers of average molecular weights of, say, 25,000 to 100,000 the ratio of fluorochrome dye molecules and of hormone molecules to the protein molecule in the conjugate may conveniently be varied within the limits of about 5:1 to 20:1 for the fluorochrome and between about 10:1 and 40:1 for the hormone.

Those skilled in the art will further recognize that chemical linkages other than those specifically illustrated above may equivalently be employed to join the hormone component to the conjugate structure. For instance, in place of the carboxymethoxyl amine, other agents having a primary amine function and a carboxy function can also be employed, so long as the amine will keto-react to form the imine structural component or linkage with the hormone entity, and the carboxy group is available for subsequent coupling as a carboxamide linkage with the dyestuff entity. Such reagents would include such variations as $$HO_2C(CH_2)_xONH_2,$$

wherein x is a small whole number, e.g. up to 8, etc.

Further, in place of succinic anhydride, to form the 11-progesterone hemisuccinate derivative, other reagents such as adipic anhydride, or side-chain-substituted succinic or adipic anhydrides may be employed, as well as aromatic anhydrides such as phthalic and trimellitic. Alternatively, in place of thioglycolic acid, other mercapto-carboxylic acids may be used to form the 6-progesterone derivatives, e.g., β-mercaptopropionic acid, mercaptosuccinic acid, thiobenzoic acid, etc. The fundamental requirement is thus that the hormone component derivative used in making the conjugate have the structure $$[hormone]-A-CO_2H$$

wherein A is the molecular residue of the reagent employed for linking the carboxylic group to the steroid nulceus.

Further, carbodiimides are only one group of coupling reagents. Other cross-linking chemical reactions may be used to couple the steroids with the carrier or the carrier with the dyes, provided suitable chemical handles have been introduced to the parent molecule. Examples thereof include for instance:

(1) Mixed anhydride techniques using tri-n-butylamine and isobutylchlorocarbonate (Erlanger et al. J. Biol. Chem. 228:713, 1958 and J. Biol. Chem. 234:1909, 1959).

(2) Diisocyanate techniques as used by Singer and Schick (J. Biophys. Biochem. Cytol. 9:519, 1961).

(3) Dihalogenated dinitrobenzene methods by Alexander et al. (Biochem. J. 52:177, 1952).

It should also be noted that the sequence of coupling is important in that the fluorochrome dyestuff should be first coupled to the carrier molecules before the hormone is attached to the carrier-fluorochrome dye complex. This will avoid possible obliteration of any physiologically functional groups of the steroid hormone, such as the hydroxyl groups of the steroid, especially when isocyanates or isothiocyanates of the fluorochrome dyestuff are used as the fluorescent indicators since the isocyanate and isothiocyanate might otherwise condense with the free hydroxyl groups of the steroids. If the latter side reaction occurs, the specificity of the final fluorescent conjugate as a receptor tracer can be affected. In other words, the final three-component conjugate should be in the form of hormone-carrier-dye, rather than in the carrier-hormone-dye or hormone-dye-carrier configuration.

It will be seen from the foregoing discussion, accordingly, that this invention has provided a novel class of agents which may be employed according to the presently disclosed method and technique for the improved determination and identification of malignant cells in a suspected mammary or other carcinoma tissue sample which possesses the estrogen or progesterone or other steroidal or hormone receptor capability.

Thus, an important clinical and diagnostic contribution has been developed to aid in the detection and identification of breast and other cancer patients having a malignancy which may be susceptible to remission by the use of hormone therapy techniques.

Of course, within the spirit and scope of the following claims, it will be apparent to those skilled in this art that the specific practice and use of the inventive contribution described herein may vary and depart from the specific embodiments used as illustrations hereinabove.

What is claimed is:

1. An agent useful for the detection of steroid hormone receptor malignant cells consisting essentially of a molecular conjugate of the formula

[hormone]—[A]—[carrier]—[fluorochrome]

wherein
(a) said [hormone] is a steroidal molecular unit covalently-bonded to —A—,
(b) said —A— is a covalently-bonded chemical linkage, and
(c) said carrier is a polyamino or polyhydroxyl hydrophylic molecular unit capable of covalent-bonding to respectively one or more of the [hormone]—A— entities and also one or more of the fluorochrome dyestuff entities, and
(d) said [fluorochrome] represents at least one dyestuff unit covalently-bonded to said carrier and capable of exhibiting visually observable color under light excitation,
and wherein the average molecular ratio of said fluorochrome dyestuff to said hormone is between about 2:1 and 1:50, and said [hormone] component of said conjugate has a concentration of about at least $10^{-2}$ M to $10^{-5}$ M in an aqueous solution at a physiological pH.

2. The molecular conjugate of claim 1 wherein said [hormone] is an estrogenic hormone of the class of 17β-estradiol, 17α-estradiol, estrone, and estriol hormones.

3. The molecular conjugate of claim 1 wherein said [hormone] is a progesterone hormone of the class of progesterone, pregnanediol, pregnanetriol and pregnenolone hormones, and the synthetic progestins of compound R5020, Norethindrone, Norethynodrel.

4. The molecular conjugate of claim 1 wherein said [hormone] is an androgenic hormone, natural or synthetic.

5. The molecular conjugate of claim 1 wherein said [hormone] is an adreno cortical hormone, natural or synthetic.

6. The molecular conjugate of claims 1, 2, 3, 4 or 5 wherein said molecular ratio is from about 2:1 to 1:25.

7. The molecular conjugate of any one of claims 1, 2, 3, 4, 5 or 6 wherein said carrier is hydrophyllic unit of the class consisting of Albumins, globulins, glutelins, prolamines, albuminoids, histones and protamines;

Nucleoproteins, glycoproteins, mucoproteins, phosphoproteins, chromoproteins, lipoproteins and metalloproteins; and Proteoses, peptones, peptides, cyclic anhydrides of two amine acids (diketopiperazines); and polyglycols or polyglycerols compounds.

8. The molecular conjugate of any one of claims 1 to 6 wherein said fluorochrome is a dyestuff of the class consisting of Auramine O, Rhodamine B, Rhodamine 3G, Acriflavine, Acridine orange, Coriphosphine, Acridine yellow, Phosphine, Benzoflavine, Thioflavine TCN, Rhodindine, Magdala red, Berberine, Quinacrine, Rivanol, tetracycline, Thiazine red R, Thiazole yellow G, Congo red, Acid fuchsin, Sulforhodamine B, Eosin Y, Primuline, Thoflavine S, Tetramethylrhodamine and dinaphtylamine sulfonic acid, and fluorescein.

9. The molecular conjugate of claim 1 wherein said [hormone] is 17β-estradiol and said carrier is bovine serum albumin and said fluorochrome dyestuff is fluorescein.

10. The molecular conjugate of claim 1, wherein said ratio of fluorochrome dyestuff to [hormone] is between about 3:2 to 1:10.

11. The molecular conjugate of claim 7, wherein said protein carrier has an average molecular weight of betwen about 25,000 and 100,000.

12. The molecular conjugate of claim 11, wherein the molecular ratio of fluorochrome dye to protein is between about 1:1 to 20:1, and the molecular ratio of [hormone] to protein is between about 10:1 to 40:1 so that the bound [hormone] component can have a concentration of about $10^{-2}$ M and $10^{-5}$ M in a stable aqueous solution of a physiological pH.

13. An agent useful for the detection of hormone receptor malignant cells consisting essentially of a molecular conjugate of (i) an estrogenic or progesterone hormone derivative of the structure [steroid]—A—$CO_2$H wherein A is the residue of the carboxylic-group-introducing reagent, (ii) a protein or polypeptide carrier coupled to said hormone through a carboxamide linkage, and (iii) a fluorochrome dyestuff coupled to said carrier through an amino group, and wherein the average molecular ratio of said fluorochrome dyestuff to said hormone is between about 2:1 and 1:50, and the conjugately-bound steroid hormone can have a concentration in the range of about $10^{-5}$ M to $10^{-2}$ M in an aqueous solution of a physiological pH.

14. An agent useful for the detection of estrogen receptor malignant cells consisting essentially of a molecular conjugate of (i) the 6-(O-carboxymethyl)oxime derivative of an estrogenic hormone, (ii) a protein or polypeptide carrier coupled to said hormone through a carboxamide linkage, and (iii) a fluorochrome dyestuff coupled to said carrier through an amino group, and wherein the average molecular ratio of said fluorochrome dyestuff to said hormone is between about 2:1 and 1:50 and the concentration bound steroid hormone in an aqueous solution is about $10^{-2}$ M to $10^{-5}$ M.

15. An agent useful for the detection of progesterone receptor malignant cells consisting essentially of a molecular conjugate of (i) the 11α-hydroxyprogesterone hemisuccinate, (ii) a protein or polypeptide carrier coupled to said hormone through a carboxamide linkage, and (iii) a fluorochrome dyestuff coupled to said carrier through an amino group, and wherein the average molecular ratio of said fluorochrome dyestuff to said hormone is between about 2:1 to 1:50, and which will yield in aqueous medium a solution having a concentration of the bound steroid hormone of about $10^{-2}$ M to $10^{-5}$ M.

16. An agent useful for the detection of progesterone receptor malignant cells consisting essentially of a molecular conjugate of (i) the progesterone-6-carboxymmethylene thioether, (ii) a protein or polypeptide carrier coupled to said hormone through a carboxamide linkage, and (iii) a fluorochrome dyestuff coupled to said carrier through an amino group, and wherein the average molecular ratio of said fluorochrome dyestuff to said hormone is between about 2:1 to 1:50, and the bound steroid hormone has a concentration of about $10^{-2}$ M to $10^{-5}$ M in an aqueous solution of a physiological pH.

17. A method for the detection and identification of suspected carcinoma tissue cells having steroidal hormone receptor characteristics, which tissues have been excised, frozen and dried in section and maintained in a chemically-unfixed condition, which method consists essentially in (1) treating said tissue section by rehydration in a phosphate-buffered substantially isotonic saline solution, having an approximately physiological pH range;

(2) coating said thus treated tissue section with a molecular conjugate of the formula (hormone)—(A)—(carrier)—(fluorochrome)

wherein (a) said (hormone) is a steroidal molecular unit covalently-bonded to —A—, (b) said —A— is a covalently-bonded chemical linkage, and (c) said carrier is a polyfunctional hydrophilic molecular unit capable of covalent-bonding to respectively one or more of the (hormone)—A— entities and also one or more of the fluorochrome dyestuff entities, and
(d) said (fluorochrome) represents at least one dyestuff unit covalently-bonded to said carrier and capable of exhibiting visually observable color under light excitation, and wherein the average molecular ratio of said fluorochrome dyestuff to said hormone is between about 2:1 and 1:50, and the conjugately-bound steroid hormone can have a concentration of about $10^{-2}$ M to $10^{-5}$ M in an aqueous solution of a physiological pH;

(3) thereafter removing said molecular conjugate coating from said tissue specimen, and rinsing the same in a phosphate-buffered substantially isotonic saline solution having an approximately physiological pH range; and thereafter examining the thus-processed tissue specimen for the presence of appearance of fluorescent dye staining of the cells therein.

* * * * *